(12) United States Patent
Kodama et al.

(10) Patent No.: US 7,666,998 B2
(45) Date of Patent: Feb. 23, 2010

(54) CELL GROWTH INHIBITOR CONTAINING ANTI-PEPT ANTIBODY

(75) Inventors: Tatsuhiko Kodama, Tokyo (JP); Takao Hamakubo, Tokyo (JP); Ryoichi Saitoh, Shizuoka (JP); Iwao Ohizumi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 393 days.

(21) Appl. No.: 10/497,900

(22) PCT Filed: Dec. 4, 2002

(86) PCT No.: PCT/JP02/12708

§ 371 (c)(1),
(2), (4) Date: Jun. 30, 2005

(87) PCT Pub. No.: WO03/047621

PCT Pub. Date: Jun. 12, 2003

(65) Prior Publication Data
US 2005/0281825 A1 Dec. 22, 2005

(30) Foreign Application Priority Data
Dec. 4, 2001 (JP) ............................. 2001-369608
Jun. 5, 2002 (JP) ............................. 2002-164834

(51) Int. Cl.
C07K 16/00 (2006.01)
A61K 39/395 (2006.01)
(52) U.S. Cl. ................................. 530/387.1; 424/130.1
(58) Field of Classification Search ........................ None
See application file for complete search history.

(56) References Cited

U.S. PATENT DOCUMENTS

| 5,500,346 | A | 3/1996 | Bright et al. | |
|---|---|---|---|---|
| 5,849,525 | A | 12/1998 | Hediger | |
| 6,270,978 | B1 | 8/2001 | Bright et al. | 435/7.1 |
| 6,713,278 | B1 | 3/2004 | Bouvier et al. | |
| 6,867,017 | B1 * | 3/2005 | Dean et al. | 435/69.1 |
| 2005/0004227 | A1 | 1/2005 | Saitoh | |
| 2005/0222391 | A1 | 10/2005 | Kodama et al. | |
| 2005/0281825 | A1 | 12/2005 | Kodama et al. | |
| 2006/0084119 | A1 | 4/2006 | Saitoh et al. | |
| 2006/0210569 | A1 * | 9/2006 | Kodama et al. | 424/155.1 |
| 2008/0040820 | A1 | 2/2008 | Kodama et al. | |

FOREIGN PATENT DOCUMENTS

| AU | 9676557 | 6/1997 |
|---|---|---|
| EP | 1142473 | 10/2001 |
| EP | 1 731 032 | 12/2006 |
| JP | 6-261761 | 9/1994 |
| JP | 8-134100 | 5/1996 |
| JP | 11-172 | 1/1999 |
| JP | 2001-197846 | 7/2001 |
| JP | 2001-139496 | 5/2005 |
| WO | WO 97/19919 | 6/1997 |
| WO | WO 98/46777 | 10/1998 |
| WO | WO 00/28016 | 5/2000 |
| WO | WO 03/033024 | 4/2003 |
| WO | WO 03/047621 | 6/2003 |
| WO | WO 03/083116 A1 | 10/2003 |
| WO | WO 03/104453 | 12/2003 |

OTHER PUBLICATIONS

Sun D. et al., "Drug Inhibition of Gly-Sar Uptake and hPepT1 Localization using hPepT1-GFP Fusion Protein", AAPS PharmSci., vol. 3(1), pp. 1-9 (2001).
Sai Y. et al., "Immunolocalization and pharmacological relevance of oligopeptide transporter PepT1 in intestinal absorption of β-lactam antibiotics", FEBS Lett, vol. 392(1), pp. 25-29 (1996).
Basu SK et al., "Development and Utility of Anti-PepT1 Anti-Peptide Polyclonal Antibodies", Pharmaceutical Research, vol. 15(2), pp. 338-342 (1998).
Gonzalez DE et al., Cancer Res., vol. 58(3), pp. 519-525 (1998).
Knutter et al., "A Novel Inhibitor of the Mammalian Peptide Transporter PEPT1", Biochemistry, vol. 40(14), pp. 4454-4488 (2001).
Mrsny RJ., "Olgiopeptide Transporters as Putative Therapeutic Targets for Cancer Cells", Pharm Res. vol. 15(6), pp. 816-818 (1998).
Nakanishi T. et al., "Cancer Cell-Targeted Drug Delivery Utilizing Oligopeptide Transport Activity", Int. J. Cancer, vol. 88(2), pp. 274-280 (2000).
Gonzalez DE et al., "An Olgiopeptide Transporter Is Expressed at High Levels in the Pancreatic Carcinona Cell Lines AsPc-1 and Capan-2[*]", Cancer Res., vol. 58(3), pp. 519-525 (1998). gano K. et al., Quantitive Structure-Intestinal Permeability Relationship of Benzamidine Analogue Thrombin Inhibitor, Bioorg Med. Chem. Lett, vol. 10(17), pp. 1939-1942 (2000).
Zhou X. et al., "Characterization of an oligopeptide transporter in renal lysosomes", Biochim Biophys Acta, vol. 1466(1-2), pp. 372-378 (2000).
Lee VHL et al., "Biopharmaceutics of transmucosal peptide and protein drug administration: role of transport mechanisms with a focus on the involvement of PepT1", J. Control Release, vol. 62(1-2), pp. 129-140 (1999).
Loisel TP et al., "Recovery of homogeneous and functional β₂-adrenergic receptors from extracellular baculovirus particles", Nat Biotechnol, vol. 15(12), pp. 1300-1304 (1997).
Mangor JT et al., "A GP64-Null Baculovirus Pseudotyped with Vesicular Stomatitis Virus G Protein", Journal of Virology, vol. 75(6), pp. 2544-2556 (2001).
Szakács G et al., "Characterization of the ATPase Cycle of Human ABCA1: Implications for Its Function as a Regulator Rather Than an Active Transporter", Biochem Biophys Res Commun, vol. 288(5), pp. 1258-1264 (2001).
Noe J et al., "Characterization of the Mouse Bile Salt Export Pump Overexpressed in the Baculovirus System", Hepatology, vol. 33(5), pp. 1223-1231 (2001).

(Continued)

Primary Examiner—Christopher H Yaen
(74) Attorney, Agent, or Firm—Fish & Richardson P.C.

(57) ABSTRACT

The present inventors extensively studied and found that an antibody binding to PepT has cytotoxic activity and inhibits cell growth. These results suggest that an antibody binding to PepT, particularly an antibody having a cytotoxic activity, can be used as a cell growth inhibitor, for example, in treating and preventing cancer.

23 Claims, 2 Drawing Sheets

OTHER PUBLICATIONS

Sakaguchi T. et al., "The Ion Channel Activity of the Influenza Virus $M_2$ Protein Affects Transport through the Golgi Apparatus", J Cell Biol., vol. 133(4), pp. 733-747 (1996).

Mikhailov MV et al., "Expression of functionally active ATP-sensitive K-channels in insect cells using baculovirus", FEBS Lett, vol. 429(3), pp. 390-394 (1998).

Su

Strehlow D. et al., "Retroviral membrane display of apoptotic effector molecules", Proc Natl Acad Sci USA, vol. 97(8), pp. 4209-4214 (2000).

Basu et al., "Screening of Anti-PepT1 Antibodies Using Indirect ELISA," *Pharmaceutical Research*, 13(9 Suppl.):S-37, Abstract No. APQ 1137 (1996).

Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus," *Virology*, 170:537-555 (1989).

Friedman et al., "Characterization of the Intestinal Transport Parameters for Small Peptide Drugs," *J. Control. Release*, 13:141-146 (1990).

Friedman et al., "Passive and Carrier-Mediated Intestinal Absorption Components of Two Angiotensin Converting Enzyme (ACE) Inhibitor Prodrugs in Rats: Enalapril and Fosinopril," *Pharm. Res.*, 6:1043-1047 (1989).

Ganapathy et al., "Proton-coupled solute transport in the animal cell plasma membrane," *Curr. Opin. Cell Biol.*, 3:695-701 (1991).

Higgins, "ABC Transporters: From Microorganisms to Man," *Annu. Rev. Cell Biol.*, 8:67-113 (1992).

Houdebine, "Transgenic animal bioreactors," *Transgenic Res.*, 9:305-320 (2000).

Kolb et al., "Insertion of a foreign gene into the β-casein locus by Cre-mediated site specific recombination," *Gene*, 227:21-31 (1999).

Lariviere et al., "Transgenic Studies of Pain and Analgesia: Mutation or Background Genotype?" *J. Pharmacol. Exp. Ther.*, 297:467-473 (2001).

Leiter, "Mice with targeted gene disruptions or gene insertions for diabetes research: problems, pitfalls, and potential solutions," *Diabetologia*, 45:296-308 (2002).

Liang et al., "Human Intestinal $H^+$/Peptide Cotransporter. Cloning, Functional Expression, and Chromosomal Localization," *J. Biol. Chem.*, 270:6456-6463 (1995).

Lindley et al., "Production of monoclonal antibodies using recombinant baculovirus displaying gp64-fusion proteins," *J. Immunol. Methods*, 234:123-135 (2000).

Liu et al., "Molecular cloning of PEPT2, a new member of the $H^+$/peptide cotransporter family, from human kidney," *Biochim. Biophys. Acta*, 1235:461-466 (1995).

Mancini et al., "Induction of Anti-Hepatitis B Surface Antigen (HBsAg) Antibodies in HBsAg Producing Transgenic Mice: A Possible Way of Circumventing 'Nonresponse'to HBsAg," *J. Med. Virol.*, 39:67-74 (1993).

Muranushi et al., "Transport Characteristics of Ceftibuten, a New Oral Cephem, in Rat Intestinal Brush-Border Membrane Vesicles: Relationship to Oligopeptide and Amino β-Lactam Transport," *Pharm. Res.*, 6:308-312 (1989).

Murray, "Genetic Modification of Animals in the Next Century," *Theriogenology*, 51:149-159 (1999).

Nakashima et al., "Kinetics and Mechanism of In Vitro Uptake of Amino-β-Lactam Antibiotics by Rat Small Intestine and Relation to the Intact-Peptide Transport System," *Biochem. Pharmacol.*, 33:3345-3352 (1984).

Ogihara et al., "Immuno-Localization of $H^+$/Peptide Cotransporter in Rat Digestive Tract," *Biochem. Biophys. Res. Commun.*, 220:848-852 (1996).

Okano et al., "$H^+0$ Coupled Uphill Transport of Aminocephalosporins via the Dipeptide Transport System in Rabbit Intestinal Brush-border Membranes," *J. Biol. Chem.*, 261:14130-14134 (1986).

Sai et al., "Selective Delivery of Peptide Anticancer Drugs via Oligopeptide Transporter Expressed in Cancer Cells," *Proceedings of the Millennium World Congress of Pharmaceutical Science*, p. 61, Abstract No. 2-2124 (Apr. 16-20, 2000).

Saito et al., "Cloning and Characterization of a Rat $H^+$/Peptide Cotransporter Mediating Absorption of β-Lactam Antibiotics in the Intestine and Kidney," *J. Pharmacol. Exp. Ther.*, 275:1631-1637 (1995).

Saito et al., "Molecular cloning and tissue distribution of rat peptide transporter PEPT2," *Biochim. Biophys. Acta*, 1280:173-177 (1996).

Satoi et al., "Genetic Immunization of Wild-Type and Hepatitis C Virus Transgenic Mice Reveals a Hierarchy of Cellular Immune Response and Tolerance Induction against Hepatitis C Virus Structural Proteins," *J. Virol.*, 75:12121-12127 (2001).

Shen et al., "Localization of PEPT1 and PEPT2 proton-coupled oligopeptide transporter mRNA and protein in rat kidney," *Am. J. Physiol.*, 276:F658-F665 (1999).

Sigmund, "Viewpoint: Are Studies in Genetically Altered Mice Out of Control," *Arterioscler. Thromb. Vasc. Biol.*, 20:1425-1429 (2000).

Steiner et al., "The PTR family: a new group of peptide transporters," *Mol. Microbiol.*, 16:825-834 (1995).

Takahashi et al., "Interaction of β-Lactam Antibiotics with $H^+$ Peptide Cotransporters in Rat Renal Brush-Border Membranes," *J. Pharmacol. Exp. Ther.*, 286:1037-1042 (1998).

Terada et al., "Characterization of Stably Transfected Kidney Epithelial Cell Line Expressing Rat $H^+$/Peptide Cotransporter PEPT1: Localization of PEPT1 and Transport of β-Lactam Antibiotics," *J. Pharmacol. Exp. Ther.*, 281:1415-1421 (1997).

Tsuchiya, "Therapeutic Antibody," Presentation, Chugai Pharmaceutical Co., Ltd., 21 pages (Jan. 21, 2003).

Blissard et al., "Baculovirus gp64 Gene Expression: Analysis of Sequences Modulating Early Transcription and Transactivation by IE1," *J. Virol.*, 65:5820-5827 (1991).

Karaki et al., "Production of anti-HLA class I alloantibodies using HLA-B51 transgenic mice," *Nihonmenekigakkaisoukai Gakujutsushuukaikiroku*, Abstract No. C61, p. 197 (1990) (English translation included).

Nishimura et al., "Expression of the Human MHC, HLA-DQw6 Genes Alters the Immune Response in C57BL/6 Mice," *J. Immunol.*, 145:353-360 (1990).

Okamoto et al., "Generation of monoclonal antibodies directed against allotypic epitopes of HLA class II antigen by utilizing HLA-DQw6 transgenic mice," *Nihonmenekigakkaisoukai Gakujutsushuukaikiroku*, Abstract No. C62, p. 197 (1990) (English translation included).

Hsu et al., "Overexpression of Human Intestinal Oligopeptide Transporter in Mammalian Cells via Adenoviral Transduction," *Pharm. Res.*, 15:1376-1381 (1998).

D'Onofrie, "Making the case for acncer prevention in the schools", Journal of School Health 59(5):225-227, 1989.

Inoue et al., "Regulation of human peptide transporter 1 (PEPT1) in gastric cancer cells by anticancer drugs", Cancer Letters 230:72-80, 2005.

Pardee, "Tumor progression—targets for differential therapy", Journal of Cellular Physiology 209(3):589-591, 2006 (abstract only).

Winter et al., "Man-made antibodies", Nature 349:293-299, 1991.

Campbell. "Monoclonal antibody technology", Elsevier Science Publishing Company, Inc., New York, pp. 1-33, 1984.

ATCC Web Catalog, "Tumor Cell Lines," www.atcc.org (2007), 15 pages.

Boublik et al., "Eukaryotic Virus Display: Engineering the Major Surface Glycoprotein of the Autographa californica Nuclear Polyhedrosis Virus (AcNPV) for the Presentation of Foreign Proteins on the Virus Surface," Biotechnology, 13 1079-1084 (1995).

"Cancer Classification," SEER Training Website, www.training.seer.cancer.gov/module_cancer_disease/unti3-categories2_by_histology (2005), 3 pages.

Garcia et al., "cDNA Cloning of MCT2, A Second Monocarboxylate Transporter Expressed in Different Cells than MCT1," The Journal of Biological Chemistry, 270: 1843-1849 (1995).

Grever et al., "The National Cancer Institute: Cancer Drug Discovery and Development Program," Seminars in Oncology, 19(6): 622-638 (1992).

Hefferon et al., "Host Cell Receptor Binding by Baculovirus GP64 and Kinetics of Virion Entry," *Virology*, 258: 455-468 (1999).

Kamada et al., "Generation of GP64-Expressing Mice and Induction of Tolerance to Budding Baculoviruses," *Nihon Bunshi Seibutsu Gakkai Nenkai Program Keon Yoshishu*, Abstract No. 1PC-162, p. 659 (2003) (Translation Provided).

Lu et al., "Characterization of a Truncated Soluble Form of the Baculovirus (AcMNPV) Major Envelope Protein Gp64," Protein Expression and Purification, 24: 196-201 (2002).

Miyasaka et al., "Characterization of Human Taurine Transported Expressed in Insect Cells Using a Recombinant Baculovirus," Protein Expression and Purification, 23: 389-397 (2001).

Monsma et al., "Identification of a Membrane Fusion Domain and an Oligomerization Domain in the Baculovirus GP64 Envelope Fusion Protein," *Journal of Virology*, 69: 2583-2595 (1995).

Monsma et al., "The GP64 Envelope Fusion Protein is an Essential Baculovirus Protein Required for Cell-to-Cell Transmission of Infection," *Journal of Virology*, 70: 4607-4616 (1996).

Ohtomo et al., "Generation of Functional Antibodies Using GP64-Expressing/CCR2 Knock-Out Mice and CCR2-Expressing Baculoviruses," Nihon Bunshi Seibutsu Gakkai Nenkai Program Keon Yoshishu, Abstract No. 1PC-164, 26:660(2003) (Translation Provided).

Seliger et al., "Analysis of the MHC Class I Antigen Presentation Machinery in Human Embryonal Carcinomas: Evidence for Deficiencies in TAP, LMP, and MHC Class I Expression and Their Upregulation by IFN-γ," Scandinavian Journal of Immunology, 46: 625-632 (1997) (Abstract).

Suzuki et al., "Effects of Retinoic Acid on Lung Smooth Muscle Cells," Meeting on Experimental Biology: Translating The Genome (Apr. 17-21, 2004) as published in *FASEB Journal*, 18(4-5): 355-356 (2004) (Abstract).

Tamura et al., "CD14 Transgenic Mice Expressing Membrane and Soluble Forms: Comparisons of Levels of Cytokines and Lethalities in Response to Lipopolysaccharide Between Transgenic and Non-Transgenic Mice,", *International Immunology*, 11:333-339 (1999).

Watanabe et al., "Enhanced Immune Responses in Transgenic Mice Expressing a Truncated Form of the Lymphocyte Semaphorin CD100," *J. Immunol.* 167: 4321-4328 (2001).

Braunagel et al., "Autographa californica Nuclear Polyhedrosis Virus, PDV, and ECV Viral Envelopes and Nucleocapsids: Structural Proteins, Antigens, Lipid and Fatty Acid Profiles," Virology, 202:315-320 (1994).

Grabherr et al., "Developments in the use of baculoviruses for the surface display of complex eukaryotic proteins," Trends in Biotechnology, 19:231-236 (2001).

Marheineke et al., "Lipid composition of *Spodoptera frugiperda* (Sf9) and *Trichoplusia ni* (TN) insect cells used for baculovirus infection," FEBS Letters, 441:49-52 (1998).

Covitz et al., "Membrane Topology of the Human Dipeptide Transporter, hPEPT1, Determined by Epitope Insertions," *Biochemistry*, 37:15214-15221 (1998).

Kawaguchi et al., "Gan Chiryo to Syukusyu: Frontiers in Cancer Treatment," 13(1):12-20 (2001).

McLaughlin, "Rituximab: perspective on single agent experience, and future directions in combination trials," *Critical Reviews in Oncology/Hematology*, 40:3-16 (2001).

Tada et al., "Complement-dependent cytolysis," *Dictionary of Immunology 3rd Edition*, 144 (1993).

Tsuruo et al., "Inhibition of Multidrug-resistant Human Tumor Growth in Athymic Mice by Anti-P-glycoprotein Monoclonal Antibodies," *Jpn. J. Cancer Res.*, 80:627-631 (1989).

Walker et al., "Substrate upregulation of the human small intestinal peptide transporter, hPepT1," *Journal of Physiology*, 507.3:697-706 (1998).

Breyer et al., "Mutational analysis of ligand binding activity of $\beta_2$, adrenergic receptor expressed in *Escherichia coli*," *EMBO J.*, 9(9):2679-2684 (1990).

Clark, M., "Antibody humanization: a case of the 'Emperor's new clothes'?," *Immunol. Today*, 21(8):397-402 (2000).

Kanamitsu, Kotai Kogalcu Nyumon, 33-6 (1994) (English translation included).

Saitoh et al., "Recovery of functional peptide transporter PepT1 in budded baculovirus fraction," *Protein Expr. Purif.*, 46(1):130-135 (2006).

Tate et al., "Molecular Chaperones Stimulate the Functional Expression of the Cocaine-Sensitive Serotonin Transporter," *J. Biol. Chem.*, 274(25):17551-17558 (1999).

U.S. Examiner Celia C. Chang, USPTO Restriction Requirement in U.S. Appl. No. 10/492,376, dated Jun. 6, 2007, 16 pages.

Fish & Richardson P.C., Response to Restriction Requirement dated Jun. 6, 2007 in U.S. Appl. No. 10/492,376, filed Jul. 6, 2007, 1 page.

US. Examiner Celia C. Chang, USPTO Office Action in U.S. Appl. No. 10/492,376, dated Sep. 17, 2007, 6 pages.

Fish & Richardson P.C., Amendment in Reply to Action dated Sep. 17, 2007 in U.S. Appl. No. 10/492,376, filed Jan. 17, 2008, 10 pages.

U.S. Examiner Celia C. Chang, USPTO Office Action in U.S. Appl. No, 10/492,376, dated Apr. 1, 2008, 10 pages.

Japanese Patent Office, International Preliminary Report on Patentability for App. Ser. No. PCT/11302/10743, dated Apr. 21, 2003, 4 pages.

Japanese Patent Office, International Search Report for App. Ser. No, PCT/JP02/10743, mailed Feb. 4, 2003, 2 pages.

Japanese Patent Office, International Preliminary Report on Patentability for App. Ser. No. PCT JP02/12708, dated Aug. 12, 2003, 6 pages.

Japanese Patent Office, International Search Report for App. Ser. No. PCT/JP02/12708, mailed Mar. 11, 2003, 4 pages.

U.S. Examiner Ian D. Dang, USPTO Restriction Requirement in U.S. Appl. 10/509,343, dated Jan. 25, 2007, 6 pages.

Fish & Richardson P.C., Response to Restriction Requirement dated Jan. 25, 2007 in U.S. Appl. No. 10/509,343, filed Feb. 26, 2007, 6 pages.

U.S. Examiner Ian D. Dang, USPTO Office Action in U.S. Appl. No. 10/509,343, dated May 16, 2007, 24 pages.

Fish & Richardson P.C. Amendment in Reply to Action dated May 16, 2007 in U.S. Appl. No. 10/509,343, filed Nov. 16, 2007, 24 pages.

U.S. Examiner Ian D. Dang, USPTO Office Action in U.S. Appl. No. 10/509,343, dated Feb. 5, 2008, 14 pages.

U.S. Examiner Ian D. Dang, USPTO Interview Summary in U.S. Appl. No. 101509,343, dated Mar. 6, 2008, 4 pages.

Fish & Richardson P.C. Amendment in Reply to Action dated Feb. 5, 2008 in U.S. Appl. No. 10/509,343, filed Mar. 5, 2009, 10 pages.

U.S. Examiner Ian D. Dang, USPTO Notice of Allowance in U.S. Appl. No. 10/509,343, dated May 27, 2009, 17 pages.

Japanese Patent Office, International Preliminary Report on Patentability for App. Ser. No. PCT/JP03/03975, dated Sep. 8, 2003, 6 pages.

Japanese Patent Office, International Search Report for App. Ser. No. PCT/JP03/03975, mailed May 6, 2003, 2 pages.

U.S. Examiner Louis D. Lieto, USPTO Restriction Requirement in U.S. Appl. No. 10/516,603, dated Dec. 28, 2005, 5 pages.

Fish & Richardson P.C., Response to Restriction Requirement dated Dec. 28, 2005 in U.S. Appl. No. 10/516,603, filed Mar. 28, 2006, 1 page.

Examiner Louis D. Lieto, USPTO Office Action in U.S. Appl. No. 10/516,603, dated Apr. 24, 2006, 15 pages.

Fish & Richardson P.C., Amendment in Reply to Action dated Apr. 24, 2006 in U.S. Appl. No. 10/516,603, filed Oct. 24, 2006, 9 pages.

Fish & Richardson P.C., Supplemental Response to Amendment filed Oct. 24, 2006 in U.S. Appl. No. 10/516,603, filed Nov. 7, 2006, 5 pages.

U.S. Examiner Marcia Stephens Noble, USPTO Office Action in U.S. Appl. No. 10/516,603, dated mar. 9, 2007, 18 pages.

Fish & Richardson P.C., Amendment in Reply to Action dated Mar. 9, 2007 in U.S. Appl. No. 10/516,603, filed Jun. 11, 2007, 10 pages.

Fish & Richardson P.C., Amendment in U.S. App. Ser. No. 101516,603, filed Sep. 10, 2007, 6 pages.

U.S. Examiner Marcia Stephens Noble, USPTO Notice of Allowance in U.S. App. Ser. No. 10/516,603, dated Apr. 25, 2008, 11 pages.

Fish & Richardson P.C., Amendment in U.S. Appl. No. 10/516,603, filed Jul. 24, 2008, 5 pages.

U.S. Examiner Marcia Stephens Noble, USPTO Office Action in U.S. Appl. No. 10/516,603, dated Jan. 27, 2009, 7 pages.

Fish & Richardson P.C., Amendment in Reply to Action dated Jan. 27, 2009 in U.S. Appl. No. 10/516,603, filed May 15, 2009,4 pages.

Japanese Patent Office, International Preliminary Report on Patentability for App. Ser. No. PCT/JP03/07071, dated Nov. 21, 2003, 7 pages.
Japanese Patent Office, International Search Report for App. Ser. No. PCT/JP03/07071, mailed Jul. 22, 2003, 3 pages.
U.S. Examiner Christopher H. Yaen, USPTO Office Action in U.S. Appl. No. 10/550,987, dated Oct. 5, 2007, 16 pages.
Fish & Richardson P.C., Amendment in Reply to Action dated Oct. 5, 2007 in U.S. Appl. No. 101550,987, filed Mar. 5, 2008, 9 pages.
U.S. Examiner Christopher H. Yaen, USPTO Office Action in U.S. Appl. No. 10/550,987, dated Jun. 13, 2008, 13 pages.
Fish & Richardson P.C., Amendment in Reply to Action dated Jun. 13, 2008 in U.S. Appl. No. 10/550,987, filed Feb. 19, 2009, 12 pages.
U.S. Examiner Christopher H. Yaen, USPTO Office Action in U.S. Appl. No. 10/550,987, dated Mar. 31, 2009, 12 pages.
European Examiner R. Rankin, European Search Report for App. Ser. No. EP 04723785.4, dated Jul. 12, 2006, 2 pages.
Japanese Patent Office, International Preliminary Report on Patentability for App. Ser. No, PCT/JP04/004331, dated Dec. 17, 2004, 5 pages.
Japanese Patent Office, International Search Report for App. Ser. No. PCT/JP04/004331, mailed Jun. 22, 2004, 2 pages.
U.S. Examiner Michael C. Wilson, USPTO Office Action in U.S. Appl. No. 10/594,690, mailed Oct. 16, 2008, 18 pages.
Fish & Richardson P.C., Amendment in Reply to Action dated Oct. 16, 2008 in U.S. Appl. No, 10/594,690, filed Apr. 16, 2009, 9 pages.
Examiner Michael C. Wilson, USPTO Final Office Action in U.S, Appl. No. 10/594,690, mailed Jun. 8, 2009, 11 pages.
Japanese Patent Office, International Preliminary Report on Patentability for App. Ser. No. PCT/JP2005/006298, dated Feb. 8, 2006, 10 pages.
Japanese Patent Office, International Search Report for App. Ser. No. PCT/JP2005/006298, mailed Jul. 12, 2005, 3 pages.
EPO Examiner John Renggll European Search Report for App. Ser. No. EP 03 73 3287, dated Jun. 22, 2009 (2 pages).
Bachmann et al., "Correlation of Tolerogenicity of a Viral Antigen with Its Immunogenicity," *The Journal of Immunology*, 158:5106-5111(1997).
Ramamoorthy et al., "Proton/peptide cotransporter (PEPT 2) from human kidney: Functional characterization and chromosomal localization," *Biochimica et Biophysica Acta*, 1240:1-4 (1995).
Steinhoff et al., "Variable Immune Response Against a Developmentally Regulated Self-Antigen," *Journal of Autoimmunity*, 12:27-34 (1999).
U.S. Examiner Ian D. Dang, USPTO Notice of Allowance in U.S. Appl. No. 10/509,343, dated Sep. 21, 2009, 7 pages.
U.S. Examiner Marcia Stephens Noble, USPTO Office Action in U.S. Appl. No. 10/516,603, dated Aug. 19, 2009, 10 pages.
Examiner F. Chambonnet, European Search Report for U.S. Appl. No. EP 05 72 7975, dated Sep. 11, 2009, 2 pages.

\* cited by examiner

CELL GROWTH INHIBITOR CONTAINING ANTI-PEPT ANTIBODY

TECHNICAL FIELD

The present invention relates to an antibody binding to PepT and a cell growth inhibitor containing the antibody as an effective ingredient thereof.

BACKGROUND ART

Mammalian animals need to take in external sources of nutrition and many transport proteins are known to exist in their cells. Many peptide transporters (peptide transport proteins; PepTs) that carry out peptide transport have been found to date (for example, J. Biol. Chem., 270(12):6456-6463, (1995); Biochim. Biophys. Acta., 1235:461-466, (1995); Mol. Microbiol., Vol. 16, p 825, (1995); Unexamined Published Japanese Patent Application No. (JP-A) Hei 6-261761; JP-A Hei 11-172; and U.S. Pat. No. 5,849,525). PepT can be classified into proteins that import peptides into cells and proteins that export peptides from cells. They can also be classified according to the different energy sources used during transport. Proton-driven PepTs, which carry out transport by utilizing protein gradient, belong to the PTR family (Mol. Microbiol., Vol. 16, p 825, (1995)). PepTs that carry out transport using ATP in the body belong to the ABC family (Annu. Rev. Cell. Biol., Vol. 8, p 67, (1992)).

There are reports that PepTs are involved in the transport of not only small-molecule peptides such as dipeptides and tripeptides, but also of pharmaceutical agents such as β-lactam antibiotics and ACE inhibitors (Ganapathy, Leibach., Curr. Biol. 3, 695-701, (1991); Nakashima et al., Biochem. Pharm. 33, 3345-3352, (1984); Friedman, Amidon., Pharm. Res., 6, 1043-1047, (1989); Okano et al., J. Biol. Chem., 261, 14130-14134, (1986); Muranushi et al., Pharm. Res., 6, 308-312, (1989); Friedman, Amidon., J. Control. Rel., 13, 141-146, (1990)).

PepT1 and PepT2 are proton-driven PepTs that contribute to the absorption of proteins and the maintenance of peptidic nitrogen sources by uptaking small-molecule peptides into cells. PepT1 and PepT2 are 12-transmembrane proteins, comprising 708 and 729 amino acids, respectively (J. Biol. Chem., 270(12):6456-6463, (1995); Biochim. Biophys. Acta., 1235:461-466, (1995); and Terada and Inui, Tanpakusitsu Kakusan Kouso., Vol. 46, No. 5, (2001)).

There are reports that PepT1 and PepT2 also transport pharmaceuticals such as β-lactam antibiotics and bestatin (Saito, H. et al., J. Pharmacol. Exp. Ther., 275, 1631-1637, (1995); Saito, H. et al., Biochim. Biophys. Acta., 1280, 173-177, (1996); and Terada, T. et al., J. Pharmacol. Exp. Ther., 281, 1415-1421 (1997)).

PepT1 is mainly expressed in the small intestine and its expression has been confirmed in the kidney and pancreas. Expression of PepT2 has been confirmed in the kidney, brain, lung, and spleen. PepT1 and PepT2 have been reported to be localized in the brush border membrane of intestinal and renal epithelial cells (Ogihara, H. et al., Biochem. Biophys. Res. Commun. 220, 848-852, (1996); Takahashi, K. et al., J. Pharmacol. Exp. Ther., 286, 1037-1042 (1998); Hong, S. et al., Am. J. Physiol. Renal. Physiol., 276, F658-F665 (1999); and Terada and Inui, Tanpakusitsu Kakusan Kouso., Vol. 46, No. 5, (2001)).

Furthermore, overexpression of PepT1 in the cell membrane of human pancreatic duct carcinoma cell lines (Cancer Res., 58, 519-525, (1998)) and the expression of PepT2 mRNA in human pancreatic duct carcinoma cell lines (Millennium World Congress of Pharmaceutical Sciences, (2000)) have been reported. However, the involvement of PepT1 and PepT2 in cancer cell growth was unclear and no discussion had been made as to whether PepT1 and PepT2 when used as target antigens against antibodies will affect cancer cell proliferation.

DISCLOSURE OF THE INVENTION

The present invention has been made in view of the above observations, aiming at providing an antibody binding to PepT and effectively inhibiting cell growth. Furthermore, this invention also aims at providing a cell growth inhibitor that contains the antibody as an effective ingredient.

The present inventors extensively studied and found that an antibody binding to PepT has cytotoxic activity and inhibits cell growth. These results suggest that an antibody binding to PepT, particularly an antibody having cytotoxic activity, can be used as a cell growth inhibitor.

Specifically, the present invention provides:

[1] a cell growth inhibitor comprising an antibody binding to PepT as an effective ingredient;

[2] the cell growth inhibitor according to [1], wherein the antibody binding to PepT has a cytotoxic activity;

[3] the cell growth inhibitor according to [2], wherein the cytotoxic activity is an antibody-dependent cell-mediated cytotoxic (ADCC) activity;

[4] the cell growth inhibitor according to [2], wherein the cytotoxic activity is a complement-dependent cytotoxic (CDC) activity;

[5] the cell growth inhibitor according to any one of [1] to [4], wherein the PepT is PepT1;

[6] the cell growth inhibitor according to any one of [1] to [5], wherein the cell growth inhibitor inhibits the growth of a cancer cell;

[7] the cell growth inhibitor according to [6], wherein the cancer cell is a pancreatic cancer cell;

[8] a method for causing toxicity to a cell, wherein the method comprises the step of administering an antibody binding to PepT;

[9] an antibody binding to PepT and having a cytotoxic activity;

[10] the antibody according to [9], wherein the cytotoxic activity is an antibody-dependent cell-mediated cytotoxic (ADCC) activity;

[11] the antibody according to [9], wherein the cytotoxic activity is a complement-dependent cytotoxic (CDC) activity;

[12] the antibody according to [9], wherein the antibody specifically binds to an extracellular region of PepT;

[13] the antibody according to [9], wherein the PepT is derived from human; and

[14] the antibody according to any one of [9] to [13], wherein the PepT is PepT1.

Firstly, the present invention provides a cell growth inhibitor containing an antibody binding to PepT as an effective ingredient.

In this invention, the phrase "containing an antibody binding to PepT as an effective ingredient" means containing an anti-PepT antibody as a major active ingredient, but it is not intended to limit the anti-PepT antibody content.

There is no particular limitation in the type of an antibody contained in the cell growth inhibitor of this invention so long as it is capable of binding to PepT. In one preferred embodiment, the antibody specifically binds to PepT. In another preferred embodiment, the antibody has a cytotoxic activity.

A cytotoxic activity in this invention includes, the antibody-dependent cell-mediated cytotoxicity (ADCC) and complement-dependent cytotoxicity (CDC). In the present invention, the CDC activity means a cytotoxic activity mediated by a complement system. The ADCC activity in the present invention means an activity to cause cytotoxicity to a target cell when a specific antibody binds to a surface antigen of the target cell, following which an Fcγ receptor-containing cell (such as immunocyte) binds to the Fc moiety of the antibody via the Fcγ receptor.

Whether an anti-PepT antibody has either ADCC activity or CDC activity can be determined by methods well known in the art (for example, Current protocols in Immunology, Chapter 7. Immunologic studies in humans, Editor, John E. Coligan et al., John Wiley & Sons, Inc. (1993)).

Specifically, effector cells, complement solution, and target cells are prepared first.

(1) Preparation of Effector Cells

Spleen is excised from a CBA/N mouse or such to isolate spleen cells in RPMI1640 medium (GIBCO). After washing cells with the same medium containing 10% fetal bovine serum (FBS) (HyClone), the cell density is adjusted to $5 \times 10^6$ cells/ml for preparing the effector cells.

(2) Preparation of Complement Solution

Baby Rabbit Complement (CEDARLANE) is diluted 10-fold in a medium containing 10% FBS (GIBCO) to prepare the complement solution.

(3) Preparation of Target Cells

Pancreatic cancer cell line (e.g., AsPc-1 or Capan-2) cells are radiolabeled by incubation with 0.2 mCi $^{51}$Cr-sodium chromate (Amersham Pharmacia Biotech) in DMEM medium containing 10% FBS at 37° C. for 1 h. Then, cells are washed three times with RPMI1640 medium containing 10% FBS, and adjusted to the cell density of $2 \times 10^5$ cells/ml to prepare the target cells.

Then, ADCC or CDC activity is measured. For ADCC activity, the target cells and anti-PepT antibodies are added (50 μl each/well) into a 96-well U-bottomed plate (Beckton Dickinson), and allowed to react on ice for 15 min. After the reaction, effector cells (100 μl) are added to each well, and the plate is incubated in a carbon dioxide gas incubator for 4 h. The final concentration of the antibody is set at 0 μg or 10 μg/ml. After incubation, the supernatant (100 μl) is collected and the radioactivity is measured via a gamma counter (COBRAIIAUTO-GMMA, MODEL D5005, Packard Instrument Company). Cytotoxic activity (%) can be calculated by the formula:

$$(A-C)/(B-C) \times 100$$

wherein A represents the radioactivity (cpm) of each sample; B represents the radioactivity of a sample comprising 1% NP-40 (Nacalai); and C represents the radioactivity of a sample comprising only the target cells.

On the other hand, for CDC activity, the target cells and anti-PepT antibodies are added (50 μl each/well) into a 96-well flat-bottomed plate (Becton Dickinson), and allowed to react on ice for 15 min. Then, the complement solution (100 μl) is added to each well, and incubated in a carbon dioxide gas incubator for 4 h. The final concentration of the antibody is set at 0 μg or 3 μg/ml. After the incubation, supernatant (100 μl) is recovered to be measured for its radioactivity with a gamma counter. The cytotoxic activity can be calculated in the same manner as the ADCC activity assay.

There are no particular limitations on the antibodies comprised by the cell growth inhibitors of the present invention, as long as they bind to the antigen. Mouse antibodies, rat antibodies, rabbit antibodies, sheep antibodies, chimeric antibodies, humanized antibodies, and human antibodies may be used appropriately. Although the antibodies may be either polyclonal or monoclonal antibodies, monoclonal antibodies are preferred from the point of view that they can stably produce homogeneous antibodies. Polyclonal and monoclonal antibodies can be prepared by methods well known to those skilled in the art.

Hybridoma cells that produce monoclonal antibodies can basically be produced using conventional techniques, described as follows: Specifically, the hybridoma cells can be prepared by (1) conducting immunization using the desired antigen or cells expressing the desired antigen, as the sensitizing antigen according to standard immunization methods; (2) fusing the obtained immunized cells with conventional parent cells by normal cell fusion methods; and (3) screening for monoclonal antibody-producing cells (hybridomas) using normal screening methods.

There is no particular limitation in the type of sensitizing antigen. For example, when PepT is the human PepT1, the human PepT1 protein, cells expressing said human PepT1 protein, partial peptides of the human PepT1 (such as ndltdhnhdgtpds (SEQ ID NO: 1), sspgspvtavtddfkq (SEQ ID NO: 2), tddfkqgqrht (SEQ ID NO: 3), apnhyqvvkdglnqkpe (SEQ ID NO: 4), kdglnqkpekgeng (SEQ ID NO: 5), scpevkvfedisant (SEQ ID NO: 6), and ksnpyfmsgansqkq (SEQ ID NO: 7)) and such can be used.

Antigens can be prepared according to methods using baculoviruses (e.g. WO 98/46777).

Hybridomas can be produced according to the method of Milstein et al. (Kohler, G. and Milstein, C., Methods Enzymol. (1981) 73: 3-46). When the antigen has low immunogenicity, immunization can be performed by linking it to a macromolecule with immunogenicity, such as albumin. Recombinant antibodies can also be used, and can be produced by (1) cloning an antibody gene from a hybridoma; (2) incorporating the antibody gene into an appropriate vector; (3) introducing the vector into a host; and (4) producing the recombinant antibodies by genetic engineering techniques (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the variable regions (V regions) of antibodies are synthesized from hybridoma mRNAs using reverse transcriptase. When DNAs encoding a V region of an antibody of interest are obtained, they are linked to DNAs encoding an antibody constant region (C region) of interest, and are then incorporated into expression vectors. Alternatively, DNAs encoding an antibody V region can be incorporated into expression vectors comprising DNAs of an antibody C region. The DNAs are incorporated into expression vectors such that expression is controlled by expression regulatory regions such as enhancers and promoters. Host cells are then transformed with these expression vectors to express the antibodies.

The anti-PepT antibody of this invention may recognize any epitope existing on the PepT molecule, without being limited to a particular one. However, because PepT is a twelve-transmembrane protein, the epitope present in the extracellular region is preferably recognized.

In the present invention, recombinant antibodies artificially modified to reduce heterologous antigenicity against humans can be used. Examples include chimeric antibodies and humanized antibodies. These modified antibodies can be produced using known methods. A chimeric antibody is an antibody comprising the antibody heavy chain and light chain variable regions of a nonhuman mammal such as a mouse, and the antibody heavy chain and light chain constant regions of a human. A chimeric antibody can be obtained by (1) ligating the DNA encoding a variable region of a mouse antibody to the DNA encoding a constant region of a human antibody; (2) incorporating them into an expression vector; and (3) introducing the vector into a host for production of the antibody.

A humanized antibody, which is also called a reshaped human antibody, is obtained by transplanting a complementarity determining region (CDR) of an antibody of a nonhuman mammal such as a mouse, into the CDR of a human antibody. Conventional genetic recombination techniques for the preparation of such antibodies are known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239, 400, and International Patent Application No. WO 96/02576). Human antibody FRs that are ligated via the CDR are selected where the CDR forms a favorable antigen-binding site. As necessary, amino acids in the framework region of an antibody variable region may be substituted such that the CDR of a reshaped human antibody forms an appropriate antigen-binding site (Sato, K. et al., Cancer Res. (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Examined Published Japanese Patent Application No. (JP-B) Hei 1-59878). Alternatively, the desired human antibody can also be obtained by using the desired antigen to immunize a transgenic animal that comprises the entire repertoire of human antibody genes (see International Patent Application WO 93/12227, WO 92/03918, WO 94/02602, WO 94/25585, WO 96/34096, and WO 96/33735). Furthermore, techniques to obtain human antibodies by panning with a human antibody library are known. For example, the variable region of a human antibody is expressed as a single chain antibody (scFv) on the surface of a phage using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors containing these sequences can be constructed, and human antibodies can be obtained. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. Known animal cells include: (1) mammalian cells such as CHO, COS, myeloma, baby hamster kidney (BHK), HeLa, and Vero cells; (2) amphibian cells such as *Xenopus* oocytes; or (3) insect cells such as sf9, sf21, and Tn5. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. By transferring the antibody genes of interest into these cells using transformation, and then culturing the transformed cells in vitro, the antibodies can be obtained.

Furthermore, the antibody may be an antibody fragment or a modified antibody thereof, as long as it binds to PepT. For example, the antibody fragment may be Fab, F (ab') 2, Fv, single chain Fv (scFv) in which Fv from H or L chains are ligated by an appropriate linker, or Diabody. More specifically, the antibody fragment is obtained by (1) treating the antibody with enzymes such as papain and pepsin; (2) transferring it into an expression vector; and then (3) expressing it in an appropriate host cell (see, for example, Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 663-669; and Bird, R. E. et al., TIBTECH (1991) 9, 132-137).

scFv can be obtained by ligating the V regions of the antibody H-chain and L-chain. In the scFv, the V regions of the H chain and L chain are ligated via a linker, and preferably via a peptide linker (Huston, J. S. et al., Proc. Natl. Acad. Sci. U.S.A (1988) 85, 5879-5883). The V regions of the scFv H chain and L chain may be derived from any of the antibodies described herein. The peptide linker used to ligate the V regions may be any single-chain peptide consisting of 12 to 19 residues. DNA encoding scFv can be amplified by PCR using as a template either the whole DNA, or a partial DNA encoding a desired DNA, selected from a DNA encoding the H chain or the V region of the H chain of the above antibody, and a DNA encoding the L chain or the V region of the L chain of the above antibody; and using a primer pair that defines the two ends. Further amplification can be subsequently conducted using the combination of DNA encoding the peptide linker portion, and the primer pair that defines both ends of the DNA to be ligated to the H chain and the L chain respectively. Once DNAs encoding scFvs are constructed, expression vectors containing the DNAs, and hosts transformed by these expression vectors, can be obtained according to conventional methods. Furthermore, scFvs can be obtained according to conventional methods using the resulting hosts. These antibody fragments can be produced in hosts by obtaining genes encoding the antibody fragments and expressing them in a manner similar to that outlined above. Antibodies bound to various types of molecules, such as polyethylene glycol (PEG), may be used as modified antibodies. Furthermore, antibodies may bind to radioisotopes, chemotherapeutics, and cytotoxic substances such as bacteria-derived toxin. In particular, radiolabeled antibodies are useful. Such modified antibodies can be obtained by chemical modifications of the resulting antibodies. Methods for modifying antibodies are already established in the art. The term "antibody" in the present invention also encompasses the above-described antibodies.

Furthermore, the antibody used in the present invention may be a bispecific antibody. The bispecific antibody may, have antigen-binding sites recognizing different epitopes on the PepT molecule, or may have one antigen-binding site recognizing PepT and the other recognizing a cytotoxic substance such as radioactive substance, chemotherapeutic agent, and cell-derived toxin. In this case, it is possible to inhibit the growth of tumor cells by directly applying the cytotoxic substance to the cells expressing PepT to specifically damage them. Bispecific antibodies can be prepared by linking HL pairs of two kinds of antibodies, or obtained by fusing hybridomas that produce different monoclonal antibodies to prepare fused cells generating bispecific antibody. Furthermore, the bispecific antibody can be generated by using genetic engineering techniques.

Antibodies expressed and produced as described above can be purified by conventional methods for purifying normal proteins. Antibodies can be separated and purified by, appropriately selecting and/or combining affinity columns such as a protein A column, or a chromatography column, filtration, ultrafiltration, salt precipitation, dialysis, and such (Antibodies A Laboratory Manual. Ed Harlow, David Lane, Cold Spring Harbor Laboratory, 1988).

Conventional means can be used to measure the antigen-binding activity of the antibodies (Antibodies A Laboratory Manual. Ed Harlow, David Lane, Cold Spring Harbor Laboratory, 1988). For example, enzyme linked immunosorbent assay (ELISA), enzyme immunoassay (EIA), radioimmunoassay (RIA), or fluoroimmunoassay may be used.

Furthermore, PepT-binding antibodies contained in the cell growth inhibitors of this invention are not particularly limited, however are preferably antibodies binding to PepTs which have the transport activity of incorporating peptides into cells using proton motive force. More preferably, they are antibodies binding to PepT1 or PepT2, and most preferably, they are antibodies binding to PepT1.

The nucleotide and amino acid sequences of PepT1 and PepT2 are already known (human PepT1: GenBank XM 007063 (J. Biol. Chem., 270(12):6456-6463, (1995)); human PepT2: GenBank XM 002922 (Biochim. Biophys. Acta., 1235:461-466, (1995)); mouse PepT1: GenBank AF 205540 (Biochim. Biophys. Acta., 1492:145-154 (2000)); and mouse PepT2: GenBank NM 021301 (Biochim. Biophys. Res. Commun., 276:734-741 (2000))).

Furthermore, a preferred antibody binding to PepT of the present invention specifically binds to the extracellular region of PepT. In this invention, the phrase "specific binding to the extracellular region" means that the antibody is able to immunologically distinguish the extracellular region of PepT from other regions. More specifically, the antibody specifically binding to the extracellular region of PepT only binds to the extracellular region but not to the intracellular region and such as well as transmembrane domains. In this invention, a preferred PepT is the human PepT. The human PepT can be not only derived from human but also obtained as a recombinant by expressing the human PepT in the baculoviral expression system. An immunogen used for obtaining antibody which binds specifically to the extracellular region can include, PepT expressed on the membrane such as cytoplasmic and viral membranes, and fragments containing the PepT extracellular region. Furthermore, regardless of the transporter activity, both PepTs with or without the transport activity can be used as immunogens. For PepT with the transporter activity, PepT expressed on the membrane such as cytoplasmic and viral membranes (for example, PepTs expressed on the Ba/F3 cell membrane and baculoviral membrane) can be used. For example, since PepT is known to incorporate glycylsarcosine into cells as a substrate, it is possible to judge whether the PepT has the transport activity or not by contacting it with [$^{14}$C]glycylsarcosine to observe the uptake thereof.

There are no particular limitations as to the cells to be targeted by the growth inhibitors, but cancer cells such as pancreatic cancer cells, liver cancer cells, lung cancer cells, esophageal cancer cells, breast cancer cells, and colon cancer cells are preferred, and pancreatic cancer cells are especially preferred. Therefore, the cell growth inhibitors of the present invention can be used for the purpose of treatment and prevention of diseases caused by cell growth, and more specifically of cancers such as pancreatic cancer.

The cell growth inhibitors of the present invention can be administered either orally or parenterally, but are preferably administered parenterally. Specific examples include injections, nasal formulations, pulmonary formulations, and cutaneous formulations. For example, injections can be administered systemically or locally by intravenous injection, intramuscular injection, intraperitoneal injection, or subcutaneous injection. Furthermore, the method of administration can be selected appropriately according to the age and symptoms of the patient. A single dose can be selected, from within the range of 0.0001 mg to 1,000 mg per kg body weight. Alternatively, the dose can be selected, from within the range of 0.001 to 100,000 mg/body for each patient. However, the dose of a therapeutic agent of the present invention is not limited to these examples.

The cell growth inhibitors of the present invention can be formulated according to standard methods (see, for example, Remington's Pharmaceutical Science, latest edition, Mark Publishing Company, Easton, U.S.A), and may comprise pharmaceutically acceptable carriers and additives. Exemplary carriers include surfactant, excipient, coloring agent, flavoring agent, preservative, stabilizer, buffering agents, suspending agents, isotonizing agent, binder, disintegrator, lubricant, fluidity promoter, and corrigent. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on.

Furthermore, the present invention provides a method for causing cytotoxicity to cells, which comprises the step of administering the antibody binding to PepT. The antibody binding to PepT has been described above as the antibody binding to PepT contained in the cell growth inhibitor of the present invention. The method of this invention can be used for treating and preventing disorders caused by cell growth, particularly cancers such as pancreatic cancer.

BEST MODE FOR CARRYING OUT THE INVENTION

Herein below, the present invention is described in more detail with reference to Examples.

1. Preparation of Anti-PepT1 Antibody 1-1. Preparation of DEF2A Antibody

Ba/F3 cells expressing the human PepT1 (Ba/F3-PepT1) were washed with PBS and suspended in PBS to a final density of $4 \times 10^7$ cells/ml. This cell suspension (0.25 ml) was intraperitoneally administered to Balb/c mice (female) for immunization. In a similar manner, immunization was repeated at one- to two-week intervals 19 times in total, followed by the twentieth immunization by administering the cell suspension into the tail vein.

Spleen cells were prepared from these mice, and fused to the mouse P3U1 cells by the common method using polyethylene glycol. Resulting cells were seeded in a 96-well plate, and cultured in a medium containing hypoxanthine, aminopterin, and thymidine (HAT medium) to select hybridomas. The culture supernatant was recovered on the ninth day from the cell fusion, and then screened by ELISA using the germinating baculovirus (BV-ELISA) expressing the human PepT1 (PepT1-BV) as an antigen to select for positive wells.

BV-ELISA was performed as follows. That is, PepT1-BV was diluted to be a concentration of 40 μg proteins/ml in PBS, and distributed in a 96-well ELISA plate (Maxisorp: Nunc) at 100 μl/well. This plate was left at standing at 4° C. overnight or more, allowing PepT1-BV to adsorb to the plate. Using this plate, ELISA was performed according to the common method.

Hybridomas were cloned by the limiting dilution method using the culture supernatant from wells judged positive. The culture supernatant of cloned cells was subjected again to BV-ELISA using the PepT1-BV, and the positive clone DEF2A was identified.

Figure 1:
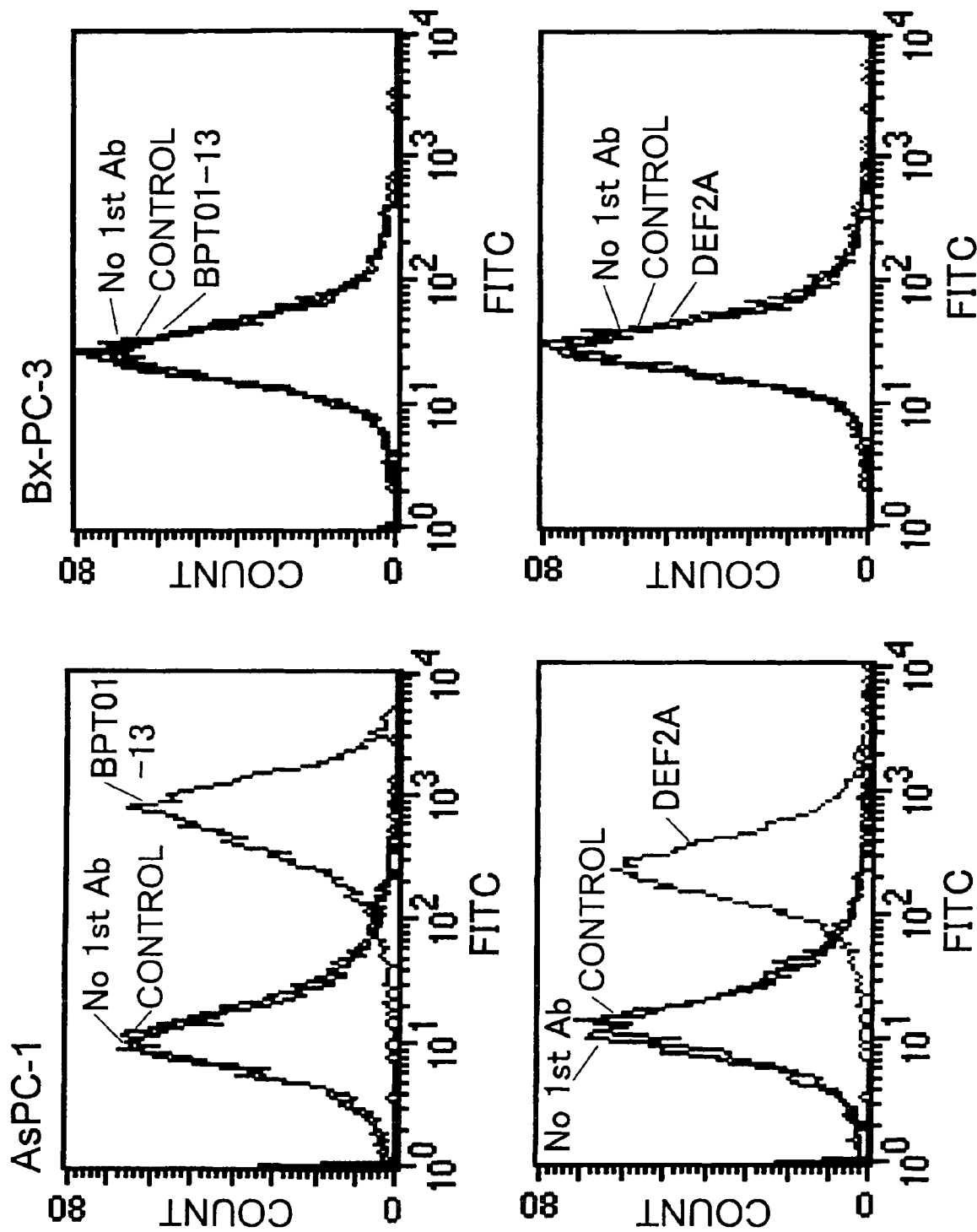
FIG. 1 depicts graphs showing the results of FACS analyses which examined the reactivity of the PepT1 antibody toward the pancreatic cancer cell lines, AsPC-1 and BxPC-3, expressing PepT1 and PepT2 at high levels, respectively.

DEF2A was cultured in an expanded scale, and the culture supernatant therefrom was examined for the reactivity toward the human pancreatic cancer cell line AsPC-1 by FACS analysis to reveal that the antibody produced by the DEF2A clone specifically reacts with AsPC-1 (FIG. 1).

1-2. Preparation of BPT01-13 Antibody

The priming of gp64 transgenic mice (Japanese Patent Application No. 2002-180351) was performed by subcutaneous injection of a suspension of PepT1-BV corresponding to 1 mg protein and 200 ng of pertussis toxin in PBS. Subsequent immunizations were carried out by subcutaneous injection of a similarly prepared PepT1-BV corresponding to 500 μg protein (containing no pertussis toxin, however). The final immunization was performed by injecting PepT1-BV (baculovirus expressing the human PepT1: Japanese Patent Application No. 2002-180351) corresponding to 250 μg protein into the mouse tail vein. Spleen cells were prepared from this mouse, and fused to the mouse P3U1 cells by the usual method using polyethylene glycol.

Screening was performed by FACS using the BaF/3-pepT1 cells. Furthermore, by FACS using the BaF/3-pepT2 cells, the monoclonal antibody "BPT01-13" specifically binding to PepT1 was established. Finally, FACS was performed with AsPC-1 and BxPC-3 cells to confirm the specific binding to PepT1 on the cancer cells (FIG. 1).

2. CDC Activity Analysis of Anti-PepT1 Antibody

The CDC activity analysis of anti-PepT1 antibody was performed using the PepT1 expression-positive and -negative pancreatic cancer cell lines (AsPC-1 and BxPC-3 cells, respectively).

Figure 2:
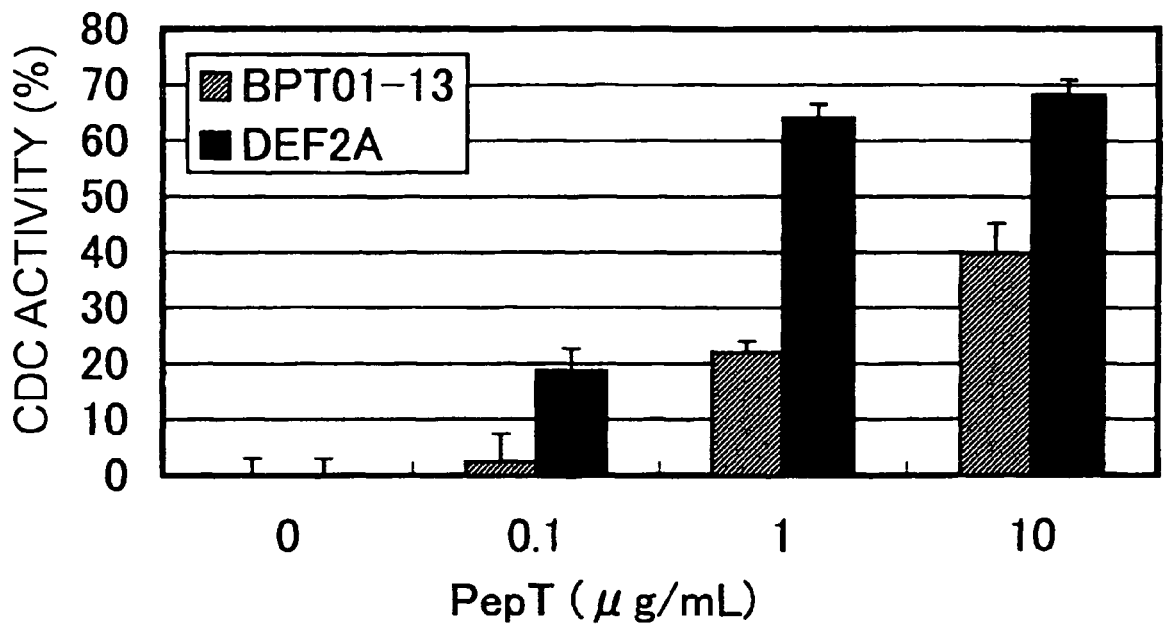
FIG. 2 depicts bar graphs showing the results of CDC activity measurements of the PepT1 antibody in the AsPC-1 and BxPC-3 cells. The upper panel shows the CDC activity toward the AsPC-1 cells while the lower panel toward the BxPC-3 cells.
Figure 2:
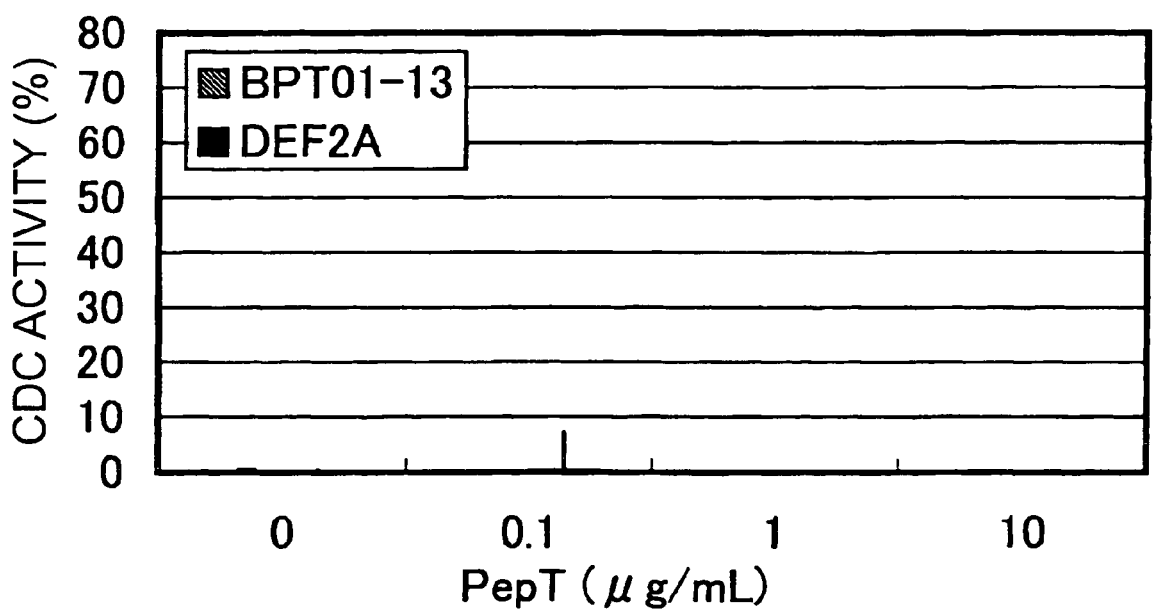

AsPC-1 cells were cultured in RPMI medium containing 20% FBS, while BxPC-3 cells in RPMI containing 10% FBS. Cells were seeded on a 96-well plate (1E4 cells/well) and cultured for two days. $^{51}$Cr (Amersham Pharmacia, CJS4) (5 μCi/well) was added to the cells and incubated for one hour to label the cells. After the cells were washed with HAV buffer (300 μl/well), 0.2 μg, 2 μg, or 20 μg/ml anti-PepT antibody (BPT01-13 or DEF2A) was added thereto (100 μl/well), and left at standing on ice for 15 min. Then, 100% baby rabbit complement (CEDARLANE, CL3441, Lot. 6213) was added thereto (100 μl/well), and the mixtures were allowed to stand at 37° C. for 90 min. After the centrifugation (1,000 rpm, 5 min, 4° C.), the supernatants (100 μl/well) were recovered to measure radioactivity with a gamma counter (Packard Instrument Company, COBRAIIAUTO-GAMMA, MODEL 505). By the following equation, CDC activity (%) was obtained:

$$CDC\ activity(\%) = (A-C) \times 100/(B-C)$$

wherein A represents the radioactivity in each well; B represents the mean radioactivity of the well comprising 2% NP-40 aqueous solution (Nonidet P-40, Nacalai Tesque, 252-23, Lot. M7M7690) (100 μl) instead of the complement; and C represents the mean radioactivity of the well comprising HAV buffer (200 μl) with neither antibody nor complement. Tests were performed in triplicates to calculate the CDC activity value and standard error (FIG. 2).

INDUSTRIAL APPLICABILITY

The present inventors have found that antibodies binding to PepT have cytotoxic activity and inhibit cell growth. These antibodies can be used as a cell growth inhibitor, for example, in treating and preventing cancer.

The invention claimed is:

1. A purified antibody that binds to PepT1, wherein the antibody contains a human antibody constant region.

2. The antibody of claim 1, wherein the antibody is not polyclonal.

3. The antibody of claim 1, wherein the antibody is human.

4. The antibody of claim 1, wherein the antibody is humanized.

5. The antibody of claim 1, wherein the antibody is chimeric.

6. The antibody of claim 1, wherein the PepT1 is a human PepT1.

7. The antibody of claim 1, wherein the antibody binds to an extracellular domain of PepT1.

8. The antibody of claim 1, wherein the antibody binds to an extracellular domain of human PepT1.

9. The antibody of claim 1, wherein the antibody induces antibody-dependent cell-mediated cytotoxic (ADCC) activity when it binds a PepT1-expressing cell.

10. The antibody of claim 1, wherein the antibody induces complement-dependent cytotoxic (CDC) activity when it binds a PepT1-expressing cell.

11. The antibody of claim 1, wherein the antibody binds to a PepT1 expression-positive cell but not a PepT1 expressionnegative cell and wherein the antibody contains a human antibody constant region.

12. A method of inhibiting cell growth, the method comprising
   providing a purified anti-PepT1 antibody; and
   contacting the antibody with a cell that expresses PepT1 on its surface, thereby inducing cytotoxic activity that results in inhibition of growth of the cell.

13. The method of claim 12, wherein the cell is a human cancer cell and the antibody contains a human antibody constant region.

14. The method of claim 12, wherein the cell is a human cancer cell and the antibody is a human antibody.

15. The method of claim 12, wherein the cell is a human cancer cell and the antibody is a humanized antibody.

16. The method of claim 12, wherein the cell is a human cancer cell and the antibody is a chimeric antibody.

17. The method of claim 12, wherein the cell is a cancer cell.

18. The method of claim 12, wherein the cell is a pancreatic cancer cell.

19. The method of claim 12, wherein the cell is selected from the group consisting of a liver cancer cell, a lung cancer cell, an esophageal cancer cell, a breast cancer cell, and a colon cancer cell.

20. The method of claim 12, wherein the cytotoxic activity is ADCC activity.

21. The method of claim 12, wherein the cytotoxic activity is CDC activity.

22. The method of claims 12, wherein the antibody is selected from the group consisting of human, humanized, and chimeric.

23. The method of claim 12, wherein the antibody is not polyclonal.

* * * * *

UNITED STATES PATENT AND TRADEMARK OFFICE
CERTIFICATE OF CORRECTION

| | | |
|---|---|---|
| PATENT NO. | : 7,666,998 B2 | |
| APPLICATION NO. | : 10/497900 | |
| DATED | : February 23, 2010 | |
| INVENTOR(S) | : Kodama et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 670 days.

Signed and Sealed this

Seventh Day of December, 2010

David J. Kappos
*Director of the United States Patent and Trademark Office*

SEQUENCE LISTING

<160> NUMBER OF SEQ ID NOS: 7

<210> SEQ ID NO 1
<211> LENGTH: 14
<212> TYPE: PRT
<213> ORGANISM: Homo sapiens

<400> SEQUENCE: 1

Asn Asp Leu Thr Asp His Asn His Asp Gly Thr Pro Asp Ser
 1               5                   10

<210> SEQ ID NO 2
<211> LENGTH: 16
<212> TYPE: PRT
<213> ORGANISM: Homo sapiens

<400> SEQUENCE: 2

```
Ser Ser Pro Gly Ser Pro Val Thr Ala Val Thr Asp Asp Phe Lys Gln
1               5                   10                  15
```

<210> SEQ ID NO 3
<211> LENGTH: 11
<212> TYPE: PRT
<213> ORGANISM: Homo sapiens

<400> SEQUENCE: 3

```
Thr Asp Asp Phe Lys Gln Gly Gln Arg His Thr
1               5                   10
```

<210> SEQ ID NO 4
<211> LENGTH: 17
<212> TYPE: PRT
<213> ORGANISM: Homo sapiens

<400> SEQUENCE: 4

```
Ala Pro Asn His Tyr Gln Val Val Lys Asp Gly Leu Asn Gln Lys Pro
1               5                   10                  15

Glu
```

<210> SEQ ID NO 5
<211> LENGTH: 14
<212> TYPE: PRT
<213> ORGANISM: Homo sapiens

<400> SEQUENCE: 5

```
Lys Asp Gly Leu Asn Gln Lys Pro Glu Lys Gly Glu Asn Gly
1               5                   10
```

<210> SEQ ID NO 6
<211> LENGTH: 15
<212> TYPE: PRT
<213> ORGANISM: Homo sapiens

<400> SEQUENCE: 6

```
Ser Cys Pro Glu Val Lys Val Phe Glu Asp Ile Ser Ala Asn Thr
1               5                   10                  15
```

<210> SEQ ID NO 7
<211> LENGTH: 15
<212> TYPE: PRT
<213> ORGANISM: Homo sapiens

<400> SEQUENCE: 7

```
Lys Ser Asn Pro Tyr Phe Met Ser Gly Ala Asn Ser Gln Lys Gln
1               5                   10                  15
```